United States Patent [19]
DeRidder

[11] Patent Number: 5,730,154
[45] Date of Patent: Mar. 24, 1998

[54] PROSTHESIS

[76] Inventor: Paul A. DeRidder, 1125 E. 17th St., Santa Ana, Calif. 92701

[21] Appl. No.: 634,836
[22] Filed: Apr. 19, 1996

Related U.S. Application Data

[63] Continuation-in-part of Ser. No. 358,695, Dec. 19, 1994, Pat. No. 5,509,891.
[51] Int. Cl.$^6$ ..................................................... A61F 5/37
[52] U.S. Cl. ........................... 128/880; 602/6; 602/22
[58] Field of Search ................................... 128/845, 846, 128/869, 877, 878, 879, 880, 881, 882; 602/5, 6, 12, 13, 17, 18, 21–23, 26

[56] References Cited

U.S. PATENT DOCUMENTS

| 2,667,868 | 2/1954 | Smyth | 602/22 |
|---|---|---|---|
| 2,823,668 | 2/1958 | Van Court et al. | 602/13 |
| 2,957,475 | 10/1960 | Drake | 602/5 |
| 4,899,737 | 2/1990 | Lazarian | 600/39 |
| 5,509,891 | 4/1996 | DeRidder | 600/38 |

Primary Examiner—Jennifer Bahr
Assistant Examiner—Samuel Gilbert
Attorney, Agent, or Firm—Plante & Strauss

[57] ABSTRACT

There is disclosed a splint prosthesis for body limbs, such as fingers, toes, arms and legs. The splint prosthesis includes a sheath, having a size and thickness which can be varied as to application, e.g., from 1 to about 3 millimeters in thickness for toe and finger splints up to several centimeters for larger body limbs such as legs and arms. The splint prosthesis has at least two longitudinal retractable stiffeners embedded within said sheath and oriented so that the stiffeners have a stable coiled configuration and a stable extended configuration. The stiffeners are formed of thin, elastic sheet material which can be rolled into a coil, and which readily unrolls. At least two stiffeners are provided, extending longitudinally along the extended sheath configuration and these are spaced apart by an angular increment which is sufficient to maintain the sheath in its extended configuration. The material of the sheath is sufficiently elastic to permit the stiffener to be rolled into a compact configuration and unrolled onto the patient's limb.

16 Claims, 2 Drawing Sheets 5,730,154

PROSTHESIS

CROSS REFERENCE TO RELATED APPLICATIONS

This application is a continuation-in-part of my application Ser. No. 08/358,695, filed Dec. 19, 1994, now U.S. Pat. No. 5,509,891.

BACKGROUND OF THE INVENTION

1. Field of Invention

This invention relates to a prosthesis to support and/or immobilize limbs, and in particular, to a splint which can be rolled into a compact package and unrolled onto a patient's limb.

2. Brief Statement of the Prior Art

Various splint prosthesis have been provided, U.S. Pat. No. 4,899,737 discloses a splint for complete circumferential immobilization of an extremity. The splint is a cylindrical rubber-like tubing in which are embedded a plurality of rod-like stiffening members 16, which may be formed of steel.

U.S. Pat. No. 3,131,691 discloses a surgical splint having a cradle and a strut which are integrally coupled at opposing ends by tubular webs 4 and 5.

Ideally, the splints should be sufficiently flexible to permit the device to be supplied in a coiled or rolled configuration which can be readily unrolled onto the patient's limb at time of use.

OBJECTIVES OF THE INVENTION

It is an objective of this invention to provide a splint prosthesis.

It is a further objective of this invention to provide the splint prosthesis in a compact configuration.

It is an additional objective of this invention to provide the splint prosthesis with support members which permit the prosthesis to be rolled and unrolled.

It is also an objective of this invention to provide the splint prosthesis with support members which, when in its unrolled configuration, provide rigidity and support for the patient's limb.

Other and related objectives will be apparent from the following description of the invention.

BRIEF STATEMENT OF THE INVENTION

This invention comprises a splint prosthesis for body limbs, such as fingers, toes, arms and legs. The splint prosthesis comprises a sheath, having a size and thickness which can be varied as to application, e.g., from 1 to about 3 millimeters in thickness for toe and finger splints up to several centimeters for larger body limbs such as legs and arms. The splint prosthesis has at least two longitudinal retractable stiffeners embedded within said sheath and oriented so that the stiffeners have a stable coiled configuration and a stable extended configuration. The stiffeners are formed of thin, elastic sheet material which can be rolled into a coil, and which readily unrolls. At least two stiffeners are provided, extending longitudinally along the extended sheath configuration and these are spaced apart by an angular increment which is sufficient to maintain the sheath in its extended configuration. The material of the sheath is sufficiently elastic to permit the stiffener to be rolled into a compact configuration and unrolled onto the patient's limb.

BRIEF DESCRIPTION OF THE DRAWINGS

The invention will be described with reference to the figures, of which.

Figure 2:
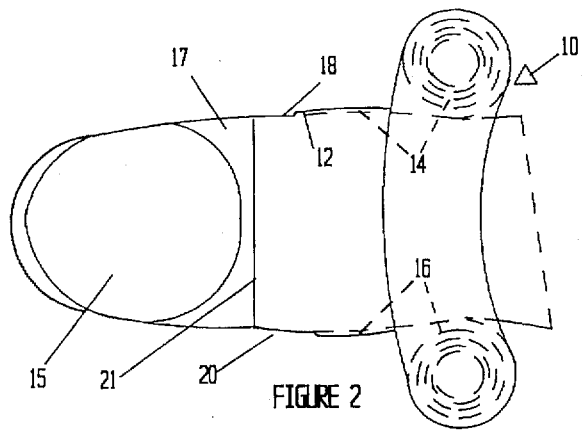
FIG. 2 is a view of the splint prosthesis as it is unrolled during application to a patient's finger.

As shown by FIG. 2, the prosthesis 10 is applied by unrolling the sheath 12 over the patient's finger 15, with the stiffeners 14 and 16 being manually uncoiled. The splint prosthesis can be readily applied over a patient's limb by inserting the limb into the coiled prosthesis, with the end 17 of the limb (finger) extending through the open end 21 of the sheath 12. The application of the splint prosthesis in this manner avoids placing any lateral or longitudinal stress on the patient's limb.

Figure 4:
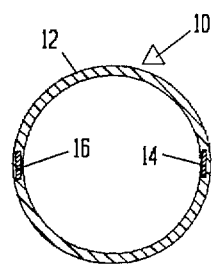
FIG. 4 is a cross sectional view along line 4—4' of FIG. 3.
Figure 3:
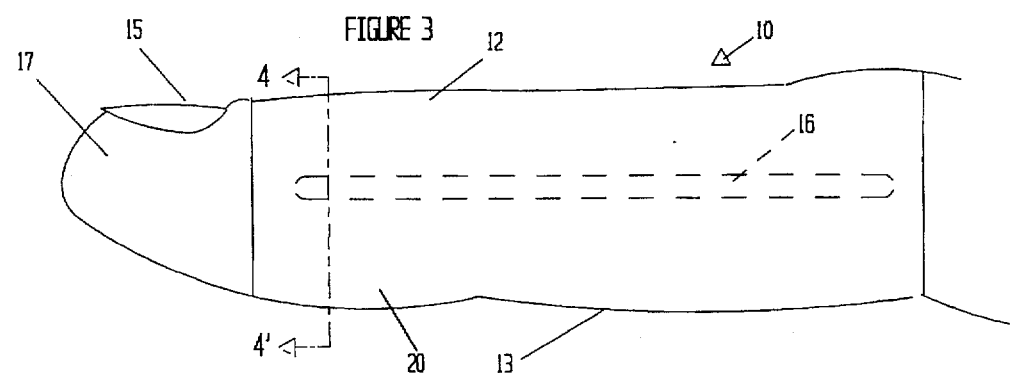
FIG. 3 is a side view of the splint prosthesis in its extended position on a patient's finger.

As shown in FIG. 3, each stiffener such as 14 assumes a stable, semi-rigid configuration, in which it will accommodate flexing along its narrow thickness, but will resist flexing along its width. The preferred cross section for the stiffeners is rectangular, as illustrated, however, a slightly arcuate cross-section can also be useful. As apparent from FIG. 4, the stiffener is entirely embedded within the sheath 12 of the splint prosthesis 10.

FIG. 3 illustrates the splint prosthesis 10 in its fully extended configuration, in which the stiffeners such as 16 extend along opposite sides of the patient's limb 15. In this configuration, the stable extended configuration of the stiffeners 14 and 16 support and contribute stiffness to the limb 15. In the illustrated embodiment, the stiffeners 14 and 16 provide support on opposite sides 18 and 20 of the limb.

Figure 5:
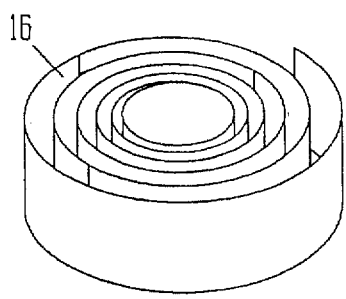
FIG. 5 is a perspective view of a suitable stiffener member in its coiled configuration.

FIG. 5 illustrates the coiled configuration of the stiffener 16, without the sheath 12. As there illustrated, the cross section of the stiffener 16 is flat, or planar. Because of the difficulty of scale, the thickness of the stiffener is minimized in the illustration.

Figure 6:
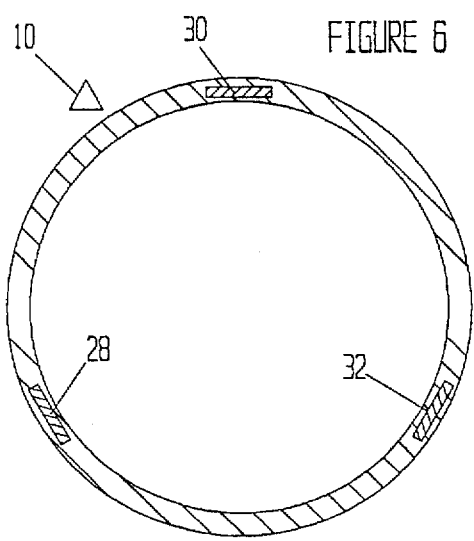
FIG. 6 is a cross sectional view of another splint prosthesis of the invention.

Various alternative forms of the splint prosthesis can be provided; as shown in FIG. 6, three stiffeners 28, 30 and 32 can be provided, one at each side and one on the top of the splint prosthesis.

Figure 7:
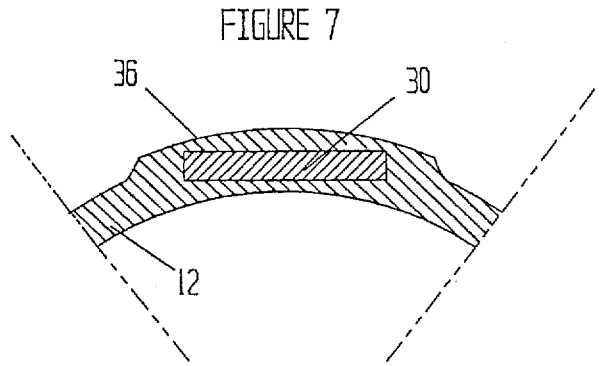
FIG. 7 is a cross sectional view of a splint 16 are rolled into coils.

In some applications, it may be desirable to limit the film thickness of the sheath in the non-reinforced areas. As shown in FIG. 7, this can be accomplished by prosthesis with stiffeners of the invention in a sheath of conventional film thickness.

DESCRIPTION OF THE PREFERRED EMBODIMENT

Figure 1:
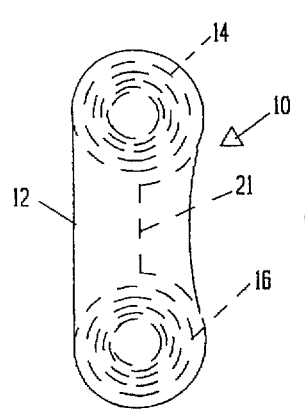
FIG. 1 is a view of the splint prosthesis in its rolled or compact configuration.

The splint prosthesis 10 of the invention is shown in FIG. 1 in its rolled or compact configuration. The splint prosthesis 10 has a thin film sheath 12 formed of an elastomer, preferably of latex rubber which has a thickness from about 0.2 to about 3 millimeters for small limbs such as fingers and toes, and a greater thickness, e.g., from 0.3 to about 3 centimeters for larger limbs such as legs and arms.

The splint prosthesis has a pair of coiled stiffeners 14 and 16, which are entirely embedded within the thin film sheath 12. The stiffeners can be located about the sheath at an angular incremental spacing from about 30° to about 180°, which is sufficient to provide rigidity to the extended configuration. It is apparent that rolling of the sheath and stiffeners requires that the material of the sheath be stretched, and the greatest stretch being required when the stiffeners 14 and 16 are on opposite sides of the sheath, i.e., at 180° incremental spacing. Alternatively, three of more stiffeners can be used, which also increases the extent of stretching required to roll and unroll the sheath 12.

The stiffeners 14 and 16 can be formed of resilient, spring-like materials, e.g., metal such as stainless steel, titanium, or of plastics such as polyethylene, polyvinyl chloride, polyesters such as Mylar, polyurethanes, etc. The stiffeners 14 and 16 have a greater width than thickness, e.g., have a width from 0.125 to about 0.5 inch, preferably from 0.2 to about 0.4 inch, and a thickness from about 0.01 to about 0.1 inch, so that they are flexible and will bend substantially only in the direction orthogonal to their thickness, as required to roll them into a coil. The splint prosthesis will stay in the illustrated, rolled configuration as the material of the sheath will resist unrolling, so the prosthesis will retain the compact configuration shown in FIG. 1, once the stiffeners 14 and increasing the sheath thickness only about the stiffeners 30, resulting in the illustrated cross-section in which the thickness of the sheath 12 in the region 36 of the stiffener 30 is from 2 to 5 times greater than the thickness of the film in the other areas 38 of the sheath 12.

The invention has been described with reference to the illustrated and presently preferred embodiment. It is not intended that the invention be unduly limited by this disclosure of the presently preferred embodiment. Instead, it is intended that the invention be defined, by the means, and their obvious equivalents, set forth in the following claims:

What is claimed is:

1. A reinforced form-supporting limb splint prosthesis which comprises:
   a. a tubular sheath formed of a latex rubber film having a thickness from 0.2 to 3 centimeters; and
   b. at least two stiffeners, each having a width to thickness ratio from about 5 to about 20 which extend entirely longitudinally along said tubular sheath and parallel to each other, spaced apart by an angular increment from 30° to 180°, and which are embedded within the thickness of said film and are formed of thin, flexible sheet material sufficiently flexible and said latex rubber being sufficiently elastic to permit said stiffeners to coil, wherein said splint prosthesis can be rolled longitudinally along said tubular sheath into a stable configuration and unrolled onto a patient's limb into a stable extended configuration with said stiffeners uncoiled and disposed longitudinally along said sheath.

2. The splint prosthesis of claim 1 wherein said film has a thickness of at least 0.5 3 millimeters.

3. The splint prosthesis of claim 1 wherein said stiffeners are formed of metal.

4. The splint prosthesis of claim 1 having a pair of said stiffeners disposed at approximately equal circumferential spacings about said splint prosthesis.

5. The splint prosthesis of claim 1 having three of said stiffeners disposed at approximately equal circumferential spacings about said splint prosthesis.

6. The splint prosthesis of claim 1 wherein said stiffeners are formed of a flexible plastic.

7. The splint prosthesis of claim 6 wherein said stiffeners are formed of a thermoplastic resin.

8. The splint prosthesis of claim 1 wherein said stiffeners are formed of a polyester.

9. A splint prosthesis which comprises:
   a. a tubular shroud formed of a latex rubber film having a thickness from 0.2 to 3 centimeters;
   b. at least two stiffeners disposed longitudinally along said tubular shroud and parallel to each other, and embedded within said film and spaced apart by an angular increment from 30° to 180°, said stiffeners being formed of thin, flexible material with cross sections having greater width than thickness and being sufficiently flexible and said latex rubber being sufficiently elastic to permit said splint prosthesis to be rolled longitudinally along said tubular sheath into a stable coiled configuration and unrolled into a stable extended configuration with said stiffeners disposed longitudinally along said sheath.

10. The splint prosthesis of claim 9 in a rolled-up configuration in which said stiffeners are coiled and said sheath is rolled up on itself.

11. The splint prosthesis of claim 9 wherein said film has a thickness from 0.5 to 1.5 millimeters.

12. The splint prosthesis of claim 9 wherein said stiffeners are formed of metal.

13. The splint prosthesis of claim 9 wherein said sheath has a pair of said stiffeners disposed at approximately equal circumferential spacings about said tubular shroud.

14. The splint prosthesis of claim 9 wherein said sheath has at least three of said stiffeners disposed at approximately equal circumferential spacings about said tubular shroud.

15. The splint prosthesis of claim 9 wherein said stiffeners are formed of a thermoplastic resin.

16. The splint prosthesis of claim 9 wherein said stiffeners are formed of a polyester.

* * * * *